United States Patent
Boam et al.

(10) Patent No.: US 10,532,320 B2
(45) Date of Patent: Jan. 14, 2020

(54) METHOD FOR IMPROVED REACTIVE MONOMER PRODUCTION WITH MEMBRANE FILTRATION

(71) Applicant: Evonik Degussa GmbH, Essen (DE)

(72) Inventors: Andrew Boam, Welwyn Garden City (GB); Yuri Bouwhuis, Princeton, NJ (US); Phillip R. James, Tenby (GB); Velichka Yordanova Koleva, Haltern am See (DE); Felix Nissen, Nottuln (DE)

(73) Assignee: Evonik Degussa GmbH, Essen (DE)

( * ) Notice: Subject to any disclaimer, the term of this patent is extended or adjusted under 35 U.S.C. 154(b) by 107 days.

(21) Appl. No.: 15/512,954

(22) PCT Filed: Sep. 22, 2015

(86) PCT No.: PCT/EP2015/071759
§ 371 (c)(1),
(2) Date: Mar. 21, 2017

(87) PCT Pub. No.: WO2016/046214
PCT Pub. Date: Mar. 31, 2016

(65) Prior Publication Data
US 2018/0361319 A1   Dec. 20, 2018

(30) Foreign Application Priority Data
Sep. 22, 2014   (EP) .................................... 14185697

(51) Int. Cl.
*B01J 8/00* (2006.01)
*C07C 7/20* (2006.01)
(Continued)

(52) U.S. Cl.
CPC .......... *B01D 61/027* (2013.01); *B01D 69/02* (2013.01); *B01D 71/68* (2013.01); *B01J 8/006* (2013.01);
(Continued)

(58) Field of Classification Search
None
See application file for complete search history.

(56) References Cited

U.S. PATENT DOCUMENTS

| 4,003,800 A | 1/1977 | Bacha et al. |
| 4,040,911 A | 8/1977 | Bacha et al. |

(Continued)

FOREIGN PATENT DOCUMENTS

| EP | 0 737 659 | 10/1996 |
| EP | 0737 660 | 10/1996 |

(Continued)

OTHER PUBLICATIONS

International Search Report for corresponding international application PCT/EP2015/071759 filed Sep. 22, 2015.

(Continued)

*Primary Examiner* — Krishnan S Menon
(74) *Attorney, Agent, or Firm* — Law Office of: Michael A. Sanzo, LLC (57) ABSTRACT

The present invention relates to production processes for reactive monomer species. The method described herein may be used in a variety of reactive monomer production processes to optimize the use of polymerization inhibitor compounds, which may lead to further advantages such as debottlenecking or elimination of process plant separation unit(s). The method provides for the separation of oligomeric/polymeric species, inhibitor compounds and reactive monomer, optionally in the presence of unreacted raw materials or solvent(s), within the production process by means of membrane filtration, particularly through the use of solvent stable membranes, and in particular by applying organic solvent nanofiltration membranes.

20 Claims, 4 Drawing Sheets

(51) Int. Cl.

| | | |
|---|---|---|
| C08F 2/40 | (2006.01) | |
| B01D 61/02 | (2006.01) | |
| B01D 69/02 | (2006.01) | |
| B01D 71/30 | (2006.01) | |
| B01D 71/68 | (2006.01) | |
| B01J 19/18 | (2006.01) | |
| B01J 19/24 | (2006.01) | |
| C07C 11/04 | (2006.01) | |
| C07C 11/06 | (2006.01) | |
| C07C 11/18 | (2006.01) | |
| C07C 15/46 | (2006.01) | |
| C07C 51/47 | (2006.01) | |
| C07C 57/04 | (2006.01) | |
| C07C 67/56 | (2006.01) | |
| C07C 69/15 | (2006.01) | |
| C07C 69/54 | (2006.01) | |
| C07C 7/144 | (2006.01) | |
| C08F 12/08 | (2006.01) | |
| C07C 253/34 | (2006.01) | |

(52) U.S. Cl.
CPC ......... *B01J 19/1893* (2013.01); *B01J 19/245* (2013.01); *B01J 19/2475* (2013.01); *C07C 7/144* (2013.01); *C07C 7/20* (2013.01); *C07C 51/47* (2013.01); *C07C 67/56* (2013.01); *C07C 253/34* (2013.01); *C08F 2/40* (2013.01); *B01D 71/30* (2013.01); *B01J 2219/0004* (2013.01); *B01J 2219/00229* (2013.01); *B01J 2219/00247* (2013.01); *B01J 2219/00254* (2013.01); *C07C 11/04* (2013.01); *C07C 11/06* (2013.01); *C08F 12/08* (2013.01); *Y02P 20/582* (2015.11)

(56) References Cited

U.S. PATENT DOCUMENTS

| | | |
|---|---|---|
| 5,174,899 A | 12/1992 | Bahrmann et al. |
| 5,215,667 A | 6/1993 | Livingston, Jr. et al. |
| 5,254,760 A | 10/1993 | Winter et al. |
| 5,288,818 A | 2/1994 | Livingston, Jr. et al. |
| 5,298,669 A | 3/1994 | Healy et al. |
| 5,395,979 A | 3/1995 | Deckman et al. |
| 5,733,663 A | 3/1998 | Scheunemann et al. |
| 6,368,382 B1 | 4/2002 | Chiou |
| 6,488,856 B2 | 12/2002 | Cossee et al. |
| 6,585,802 B2 | 7/2003 | Koros et al. |
| 6,755,900 B2 | 6/2004 | Koros et al. |
| 7,601,263 B2 | 10/2009 | Ebert et al. |
| 8,128,804 B2 | 3/2012 | Weyler et al. |
| 9,539,549 B2 | 1/2017 | Haensel et al. |
| 2005/0027150 A1 | 2/2005 | Eldin et al. |
| 2006/0135760 A1 | 6/2006 | Boam et al. |
| 2012/0279922 A1 | 11/2012 | Haensel et al. |
| 2013/0020262 A1 | 1/2013 | Bowden et al. |
| 2013/0112619 A1 | 5/2013 | Livingston et al. |
| 2014/0275465 A1* | 9/2014 | Garikipati .......... C08G 18/3206 528/68 |
| 2017/0157567 A1 | 6/2017 | Livingston et al. |

FOREIGN PATENT DOCUMENTS

| | | |
|---|---|---|
| GB | 2 369 311 | 5/2002 |
| GB | 2 373 743 | 10/2002 |
| GB | 2 437 519 | 10/2007 |
| JP | 59-225705 | 12/1984 |
| JP | 62-136212 | 12/1985 |
| JP | 2009143826 | 7/2009 |
| WO | WO 99/48896 | 9/1999 |
| WO | WO 2012/010889 | 1/2009 |
| WO | WO 2011/017797 | 2/2011 |

OTHER PUBLICATIONS

Written Opinion of the International Searching Authority for corresponding application PCT/EP2015/071759 filed Sep. 22, 2015.
International Preliminary Report on Patentability for corresponding international application PCT/EP2015/071759 filed Sep. 22, 2015.
Letter from Applicant during national stage under the PCT Direct provisions of the EPO dated Sep. 22, 2015.
European Search Report and Opinion for EP 14 18 5697 (European counterpart of U.S. Appl. No. 15/512,954), filed Sep. 22, 2014.
Toh, et al., In search of a standard method for the characterisation of organic solvent nanofiltration membranes, *Journal of membrane Science* 291(1-2):120-125 (Mar. 2007).
Vandezande, et al., "Solvent resistant nanfiltration separating on a molecular level," *Chem. Soc. Rev.* 37:365-405 (2008).

* cited by examiner

Figur 4c:

Figur 4d:

Figur 4e:

Figur 5:

Figur 6:

METHOD FOR IMPROVED REACTIVE MONOMER PRODUCTION WITH MEMBRANE FILTRATION

CROSS REFERENCE TO RELATED APPLICATIONS

The present application is US national stage of international application PCT/EP2015/071759, which had an international filing date of Sep. 22, 2015 and which was published in English on Mar. 31, 2016. Priority is claimed to European application 14185697.1, filed on Sep. 22, 2014. The priority application is hereby incorporated by reference in its entirety.

The present invention relates to production processes for reactive monomer species. The method described herein may be used in a variety of reactive monomer production processes to optimise the use of polymerisation inhibitor compounds, which may lead to further advantages such as debottlenecking or elimination of process plant separation unit(s). The method provides for the separation of inhibitor compounds and reactive monomer, optionally in the presence of oligomeric/polymeric species, unreacted raw materials or solvent(s), within the production process by means of membrane filtration, particularly through the use of solvent stable membranes, and in particular by applying organic solvent nanofiltration membranes.

The plastics industry is a significant sector of the chemical process industries, manufacturing>280 million tons of material per year in 2011 ("Plastics—the Facts 2012: An analysis of European plastics production, demand and waste data for 2011", (2012), published by PlasticsEurope (Brussels, Belgium)). A large fraction of the plastics industry relies on polymers produced from reactive monomers such as the vinyl monomers. Vinyl monomers are a key raw material for the plastics industry, and have been commercially available for more than 75 years. During that time, the manufacturing processes for making monomers have become very efficient, with advances across all aspects of the reaction, separation (distillation) and storage steps of production.

State-of-the art monomer production plants typically use several distillation columns, arranged in series and parallel, to provide polymer-grade monomers. These processes provide polymer grade monomer as the output from the monomer column, and the monomer is subsequently stabilised for storage and transportation. Though distillation is the current best practice for monomer purification and used throughout the monomer industry, there are several well-known issues:

- distillation is highly energy intensive due to the need to evaporate and condense the material that passes overhead in each distillation column;
- if the compound(s) being distilled are thermally sensitive then they may be degraded or destroyed during the distillation which can lead to increased levels of fouling on column internals and heat exchange surfaces;
- to remove small amounts of high boiling compounds requires all the volatile (low boiling) compounds in the feed to be evaporated and condensed, which can be an especially energy-intensive operation;
- in the specific case of reactive monomers, increased quantities of free radicals at higher temperature mean that inherently there will always be some polymer formation during distillation;
- in the specific case of reactive monomers, it is desirable to reduce the distillation temperature (i.e. operate at sub-ambient pressure) to reduce polymer formation however operating at sub-ambient pressure increases the likelihood of air (oxygen) ingress which in turn will lead to peroxide formation and this is both a potential safety risk and an additional source of radicals leading to increased levels of polymer formation.

In addition to the issues related to inherent radical polymerisation of vinyl monomers, plant upsets can lead to unwanted polymerisation within the monomer production plant and ultimately when a plant shuts down significant revenues are lost (e.g. a 500,000 t/y polymer plant will typically lose revenue of about €1 million per day).

In order to minimise the probability of a plant shut down due to either a process upset or fouling-related problems due to inherent polymerisation, most vinyl monomer production plants will use inhibitors within their production process to limit the amount of polymerisation that takes place.

The two topics that must be addressed by inhibitors are
- that under typical reaction and distillation conditions (elevated temperature) many vinyl monomers will spontaneously generate the free radicals required to initiate polymerisation, and
- should the monomer production plant shut down for any reason then there is the potential for polymerisation to occur within the vessels, pipework and columns which could completely block the plant.

Consequently, there has been considerable work over the years to develop inhibitor systems.

The main characteristic of inhibitors is that they offer fast reaction kinetics with free radicals, such that the free radicals are constantly being reacted to stable compounds and polymerisation does not initiate. Usually, inhibitors are continuously dosed into the separation section of the monomer production plant to prevent or minimise or at least slow down polymer formation. If an inhibitor system is not used or the dosage is sub-optimal then this will lead to fouling, i.e. a build-up of tar-like polymeric species or other insoluble deposits on for example heat exchange surfaces or column internals. Fouling is one of the most common problems in the manufacturing of petrochemicals and in particular of vinyl monomers, as it leads to reduced efficiency of the production process. Standard solutions to this problem are to reduce throughput, reduce process temperatures, and to redesign the plant. Although such solutions may reduce fouling, they may also reduce productivity or involve capital investment. If the fouling is severe enough, the plant will have to be shut down for cleaning and maintenance, leading to revenue loss. With a well-optimised inhibitor system the intervals between maintenance shut-downs can be of the order 18+ months, however with a sub-optimal inhibitor system maintenance may need to be carried out every 3-6 months. Thus there is a driver to develop and utilise inhibitor schemes that are as effective as possible.

Retarders are a special sub class of inhibitors, however their primary role is to prevent polymerisation in the case of an unplanned plant shut-down rather than react away the free radicals constantly produced during normal plant operation. In an unplanned shutdown the monomer stays in the plant because the utilities may have failed. In this case it may not be possible to pump out the monomer or cool it. Retarders have much slower kinetics with free radicals than other inhibitors, so other inhibitors are rapidly consumed in the case of a plant shut-down. The slow reaction kinetics of retarders does not completely prevent polymer formation, however the retarder(s) will maintain a degree of inhibition activity over periods of several hours while the plant is re-started or emptied, depending on the nature of the shutdown, preventing large-scale polymerisation. As retarders are consumed slowly (compared to other inhibitors) during normal plant operation, there is thus a need to effectively maintain a minimum concentration of retarder within the process without excessive losses of retarder during the monomer separation process. Furthermore, in some cases, such as styrene monomer production, the retarder compounds are highly toxic (e.g. DNBP (2,4-dinitro-6-sec-butylphenol)) and minimising handling/consumption of the retarder is a high priority for the monomer producer. Thus there is a driver to develop retarder schemes that consume as little retarder as possible during normal operation.

Membrane processes have been widely applied to a range of separations of species of varying molecular weights in both liquid and gas phases (see for example "Membrane Technology and Applications" $2^{nd}$ Edition, R. W. Baker, John Wiley and Sons Ltd, ISBN 0-470-85445-6).

Nanofiltration is predominantly applied to the filtration of aqueous fluids. Organic solvent nanofiltration (OSN) membranes are also available and are used in applications within the chemical process industries. Example applications of OSN are highlighted in the review by P. Vandezande, L. E. M. Gevers and I. F. J. Vankelecom., "Solvent resistant nanofiltration: separating on a molecular level", Chem. Soc. Rev., 2008, 37, 365-405) and specific examples from the patent literature including solvent exchange, catalyst recovery and recycling, purifications, and concentrations. U.S. Pat. Nos. 5,174,899; 5,215,667; 5,288,818; 5,298,669 and 5,395,979 disclose the separation of organometallic compounds and/or metal carbonyls from their solutions in organic media. UK Patent No. GB 2,373,743 describes the application of OSN to solvent exchange; UK Patent No. GB 2,369,311 describes the application of OSN to recycle of phase transfer agents, and; European Patent Application EP1590361 describes the application of OSN to the separation of synthons during oligonucleotide synthesis. Additional benefits of applying OSN as a separating technique include: relatively low operating pressures, high permeate fluxes, low energy consumption, and low operation and maintenance costs associated therewith. Despite these benefits and the growing commercial use of OSN, there are a very limited number of publications relating to OSN separations and reactive monomers—for instance, U.S. Pat. No. 6,488,856 (Cossee et al.) to Shell claims the separation of higher molecular weight components (>5,000 g/mol) from dicyclopentadiene (a reactive monomer) via organic solvent nanofiltration membranes but does not teach the use of inhibitors and methods of efficiently using inhibitors based on membrane separation.

The discussion of the state of the art exhibits that there remains a need for technologies that will improve the utilisation of inhibitor compounds during reactive monomer production, and the invention of this disclosure aims to provide a method for efficiently utilising inhibitor compounds through the use of organic solvent nanofiltration membranes.

Object of the present invention therefore was to provide an apparatus and a process for manufacture of reactive monomers without the problems of the prior art or having the problems of the prior art only to a reduced degree.

A special problem of the present invention was to provide an apparatus and/or a process which is less energy intensive compared to the prior art processes.

Another special problem of the present invention was to provide an apparatus and/or a process which is able to produce thermally sensitive reactive monomers with a reduced degree of degradation of the reactive monomer during manufacture.

A further special problem of the present invention was to provide an apparatus and/or a process wherein the suppression of oligomer and/or polymer formation during production and/or purification of the reactive monomer is optimized.

Also a special problem of the present invention was to provide an apparatus and/or a process with a reduced level of fouling.

In another special problem of the present invention an apparatus and/or a process should be provided with optimized intervals between maintenance shut-downs.

To optimize the use of inhibitors, in particular to avoid unnecessary losses, during production and purification of the reactive monomer was also a special problem of the present invention.

Finally a special problem of the apparatus and/or process of the present invention was to find a solution that can be integrated in, respectively that can be carried out on, existing plants with minimum effort.

Further special problems not explicitly mentioned here, become obvious in view of the prior art section, description, examples, figures and claims of this invention.

The inventors surprisingly found out that it is possible to replace one or more purification units, especially distillation devices, in a conventional purification apparatus/process for manufacture of reactive monomers with a membrane separation unit. This not only solves the energy problems and the problems with thermal degradation of the reactive monomers. The inventors surprisingly found out, that it is possible to separate unreacted inhibitors from reactive monomers via membrane separation, which allows recycling of said unreacted inhibitors. This was especially surprising since reactive monomers and inhibitors might have comparable molecular weight and polarity. It was thus not foreseeable, that inhibitors can be recycled in a very smooth and economic way.

Subject of the present invention therefore is an apparatus according to claim 1 and a process according to claim 8. Special and preferred embodiments are claimed in the dependent claims respectively are described in the following description, examples and figures of the present invention.

The terms and definitions used in the present application and as clarified herein are intended to represent the meaning within the present disclosure. The patent and scientific literature referred to herein and referenced above is hereby incorporated by reference. The terms and definitions provided herein, if in conflict with terms and/or definitions incorporated by reference, are the terms and definitions that should be used for interpreting the present disclosure.

The singular forms "a," "an," and "the" include plural reference unless the context dictates otherwise.

"%" means "% by weight" unless the context dictates otherwise.

The terms "approximately" and "about" mean to be nearly the same as a referenced number or value. As used herein, the terms "approximately" and "about" should be generally understood to encompass±30% of a specified amount, frequency or value.

The term "reactive monomers" as used herein comprise all organic molecules which can be used as raw materials in polymerization reactions, preferably in radical polymerizations, and which become part of the polymer backbone during the polymerization reaction. Preferred reactive monomers are vinyl monomers. Especially preferred monomers are styrene, (meth)acrylic acid and (meth)acrylic acid esters, acrylonitrile, butadiene, isoprene, chloroprene, vinyl acetate, ethylene and propylene.

The term "alkyl" as used in this disclosure shall be taken to comprise unbranched as well as branched alkyl.

The term "inhibitor" as used in this disclosure shall be taken to mean a compound that prevents the reactive monomer from polymerizing or minimizes or at least slows down polymerization. More specifically, an "inhibitor" is a compound that will convert free radicals to stable species; elimination of free radicals prevents radical polymerization from occurring or at least slows down radical polymerization. The cause of initiation is normally thermal decomposition of the monomer, but other reasons like contaminants such as for example air and peroxides, which act as polymerization initiators, can also cause the same effect. In the present invention, the term "inhibitor" shall also be taken to encompass mixtures of more than one "inhibitor".

Inhibitors also encompass retarders, which are a special sub group of inhibitors. The term "retarder" as used in this disclosure shall be taken to mean a compound that will convert free radicals to stable species but that has slower reaction kinetics compared to other inhibitors. Thus, less "retarder" than "inhibitor" is consumed over time compared to other inhibitors, due to the kinetics. In the present invention, the term "retarder" shall also be taken to encompass mixtures of more than one "retarder".

The term "nanofiltration" as used in this disclosure shall be taken to mean a synthetic membrane that provides a nominal molecular weight cut-off in the range 150 Da to 1,500 Da, where nominal molecular weight cut-off means the molecular weight at which the membrane provides a 90% rejection of a series of polystyrene oligomers (for example polystyrene polymer standards nominal Mp of 1,000 (part number PL2012-3010) and nominal Mp 580 (part number PL2012-2010) from Agilent Technologies) according to the method described in See Toh et al, (Journal of Membrane Science, 291(1-2) (2007), 120-125). Nanofiltration membranes differ from reverse osmosis membranes (molecular weight cut-off below 100 Da), ultrafiltration membranes (molecular weight cut-off in the range 2,000 Da to 1,000,000 Da) and microfiltration membranes (molecular weight cut-off more than 1,000,000 Da).

The term "rejection" is defined by equation (1), where $C_{Pi}$ is the concentration of species i in the permeate solution, "permeate" being the liquid which has passed through the membrane, and $C_{Ri}$ is the concentration of species i in the retentate solution, "retentate" being the liquid which has not passed through the membrane. It will be understood by one skilled in the art that a rejection of 0% implies that the membrane offers no separation of species i, and a rejection of 100% implies that species i is completely retained. It will be further recognised by one skilled in the art that provided the rejection of species A does not equal the rejection of species B then the species can be fractionated, as defined herein.

$$R_i = \left(1 - \frac{C_{Pi}}{C_{Ri}}\right) \times 100\% \quad (1)$$

The apparatus for production of reactive monomers according to the present invention, as for example shown in FIGS. 1 to 4e, comprises
  a. at least one inhibitor feed port (not shown in the Figures),
  b. a primary purification unit, herein after called "PPU", separating a feed stream comprising reactive monomers into a reactive monomer enriched stream, herein after called "RM-stream 1", and a reactive monomer depleted stream, herein after called "RM-depleted stream". Enriched means that the concentration of the reactive monomer in RM-stream 1 is higher than in the feed stream of the PPU and depleted means, that the concentration of the reactive monomer in the RM-depleted stream is lower than in the feed stream of the PPU,
  c. an inhibitor separation unit, herein after called "ISU", separating RM-stream 1 or an intermediate modified RM-stream 1, into a stream enriched in the reactive monomer, herein after called "RM-stream 2" and another stream enriched in inhibitors and depleted in reactive monomers, herein after called "inhibitor stream". Enriched means, that the concentration of reactive monomers in RM stream 2 respectively that the concentration of inhibitors in the inhibitor stream is higher than in the feed stream of the ISU.

The apparatus of the present invention is designed such that the "inhibitor stream" is recycled to at least one inhibitor feed port and that the ISU is a membrane separation unit. The feed stream comprising reactive monomers for the PPU is preferably obtained from a source that is part of the inventive apparatus as show in FIGS. 1 to 4e. It, however, can also be obtained from an independent apparatus/plant. It can be a raw material stream as obtained from a reactive monomer production unit "RMPU" or a raw material stream obtained from a RMPU that is pre-treated/pre-purified before reaching the PPU.

In case the source for the feed stream comprising reactive monomers for the PPU is part of the inventive apparatus, the apparatus comprises a RMPU as shown in FIGS. 1 to 4e. In FIGS. 1 to 4e the raw material stream of the RMPU is directly forwarded to the PPU. This is the preferred case when the raw material stream obtained from the RMPU is a liquid. There are, however, processes known in the art, for example in US 2005/0027150A1, wherein a gaseous or gas/liquid raw material stream is obtained from the RMPU. In such a case it is preferred that the raw material stream is condensed and/or pre-purified before it is fed into the PPU, as shown in US 2005/0027150A1, FIG. 1, wherein devices 6 correlates to the "RMPU" of the present invention, 10 represents a "Condensor", 14 represents "Pre-purification Unit" and 22 correlates to a "PPU").

In case the source of the feed stream for the PPU is not part of the inventive apparatus, a raw material stream including at least one reactive monomer is produced in an independent RMPU. Said raw material stream, optionally pre-purified or condensed as in US 2005/0027150A1, can be feed continuously or batch wise into the apparatus of the present invention. In such cases it is preferred that the apparatus of the invention comprises a storage tank for the raw material (instead of the RMPU shown in FIGS. 1 to 4e) and/or that it comprises a connection, preferably a pipe, with the apparatus producing the raw material stream.

RMPUs are well known devices and the processes for manufacture of the reactive monomer are also well known in the art. They preferably consist of at least one reactor, including its peripheral devices like heating/cooling devices, steering devices, condensing devices, raw material feeding devices etc., wherein the raw materials for the reactive monomer are reacted. Preferred reactors are gas-phase reactors, tubular reactors or stirred reactors or fixed bed reactors. They can be implemented as batch or continuous production units respectively process(es). The RMPU used is not critical for the present invention which is focused on the treatment and purification of the raw material stream obtained from the RMPU.

The raw material stream obtained from the RMPU and also the feed stream comprising reactive monomers for the PPU comprises at least one reactive monomer and at least one compound selected from the group consisting of unreacted raw materials for the reactive monomer production, side products of the reactive monomer production, polymers, oligomers, inhibitors, catalysts and solvents. An example for a raw material stream composition can be found in US 2005/0027150 A1, par. 3.

An inhibitor feed port is an inlet opening of a production or separation device or a pipeline etc. of the inventive apparatus through which one or more inhibitor(s) or at least a part or all of the recycled inhibitor stream or a mixture thereof can be fed. The apparatus or process of the present invention may comprise one or more inhibitor feed port(s) which might be located at different positions within the apparatus or process.

Inhibitor feed ports can principally be arranged anywhere in the apparatus or process of the present invention, preferably anywhere at or after the RMPU. Since the inhibitors are added to prevent polymerization due to free radicals formed from the reactive monomers, at least one inhibitor feed port is preferably located at an early process stage downstream of the RMPU and/or at the RMPU itself. It is preferred to have at least one inhibitor feed port located between the RMPU and the PPU. Another preferred option is to arrange one or more inhibitor feed port(s) at the PPU and/or within the PPU.

If more than one inhibitor is added to the apparatus or is used in the process of the invention, they can be added simultaneously or individually via the same or different feed ports. It is also possible to feed the whole amount of inhibitor at once or to split it off. Preferably fresh inhibitors are added continuously.

The arrangement of inhibitor feed ports in an apparatus or process for manufacture of reactive monomers is known in the art and a man skilled in the art will easily find alternatives to the set-ups described above or shown in the Figures. Such alternatives are part of the present disclosure, too.

The PPU is used for a crude purification of the reactive monomer. It usually comprises or consists of one or a series of distillation device(s), preferably 2 or 3 devices.

The PPU produces RM-stream 1 and the RM depleted stream, as explained above. RM depleted stream mainly comprises at least one component selected from the group consisting of unreacted raw materials, side products of the reactive monomer production and solvents. It can also comprise some amounts of the reactive monomers, inhibitors and polymers formed in or upstream of the PPU. The RM depleted stream can be forwarded to further separation units (not shown in the Figures) splitting it off into its components. Some of the components of the RM depleted stream, for example solvents or reactive monomers or initiators, if present, or unreacted raw materials, can be recycled or otherwise reused; others will preferably be disposed. It is also possible to dispose the whole RM depleted stream.

RM stream 1 is preferably forwarded directly or via intermediate modification to the ISU. "Intermediate modification" preferably means, that RM stream 1 is fed to a separation unit or a series of separation units and that one of the streams coming out of said separation unit or series of separation units is forwarded to the ISU (examples are shown in FIGS. 2a, 3 and 4a to 4e). If intermediate modification is done, it is preferred that the stream forwarded to the ISU comprises the main amount of remaining unreacted inhibitors, compared to the feed stream of the separation unit producing this stream. "Intermediate modification", however, may also mean, that RM stream 1 is modified by addition or exchange of chemical substances, like solvents, inhibitors etc. For example the inhibitor recycling stream or at least a part of it can be fed to RM stream 1. Combinations of the measures described above are also possible to "modify" RM stream 1

Figure 3:
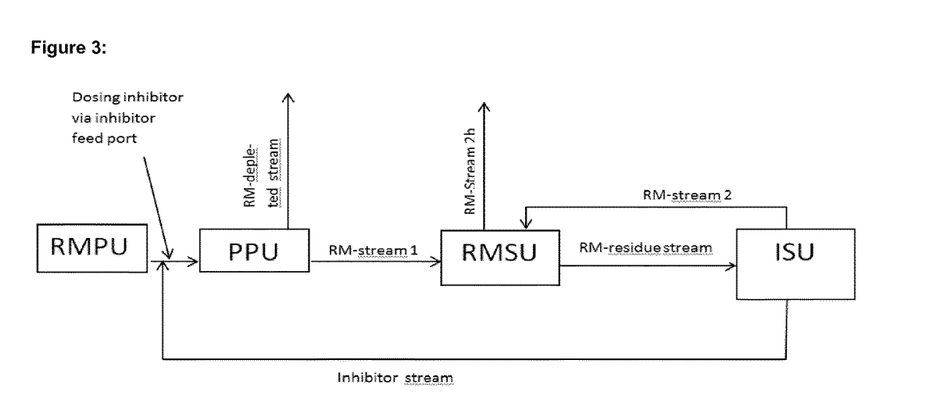
FIG. 3: Apparatus and process for production of reactive monomers with inhibitor recycling. A primary purification unit and a reactive monomer separation unit are arranged upstream of an inhibitor separation unit (inhibitor feed port not shown in the Figure)

In special but also preferred variants of the present invention, RM stream 1 is purified from oligomers and/or polymers in a "polymer separation unit", herein after called "PSU", before it is forwarded to the ISU (see FIG. 2a) or the main amount of reactive monomers is separated from RM stream 1 in a "reactive monomer separation unit", herein after called "RMSU", and only the residue stream of said RMSU, comprising a minor amount of reactive monomer and the main amount of inhibitor, compared to the feed stream of the RMSU, is forwarded to the ISU (see FIG. 3). Combinations of these preferred processes are also possible. Some preferred combinations are shown in FIGS. 4a to 4e. Alternative combinations, like an apparatus or process with two PSUs at different locations, not shown in the Figures, are possible and are also encompassed by the present invention.

The ISU is a membrane separation unit and is used to separate most of the unreacted inhibitors from its feed stream. This enables recycling of unreacted inhibitors via the inhibitor stream. As will be explained in more detail below, in a preferred process variant of the present invention, it is possible to use an excess of inhibitors to achieve an optimal suppression of polymer formation. This is only possible in an economic way with the present invention because unreacted inhibitors are recycled.

A second stream obtained from the ISU is RM stream 2. RM stream 2 may be withdrawn from the apparatus (see for example FIG. 1 or 4d or 4e) or further processed and then withdrawn from the apparatus (see for example FIG. 2b) or otherwise further processed or it may be recycled within the apparatus (see for example FIGS. 3 and 4 a to c).

As indicated before, examples of special but also preferred set-ups of the apparatus and process of the invention are given in FIGS. 2 to 4e. Depending on the required purity of the reactive monomer and the amount of polymers and/or oligomers formed during work up of the reactive monomer, a man skilled in the art is able to select one of these preferred alternatives respectively to find variants of these preferred alternatives, not explicitly described in the present disclosure.

In a first special and preferred embodiment the apparatus and process of the present invention comprises at least one "polymer separation unit" (PSU). Said PSU produces a "polymer/oligomer waste stream", which is usually disposed and a second stream, depleted in polymers and/or oligomers, compared to the feed stream of the PSU.

PSUs are especially useful in cases where the formation of polymers/oligomers cannot be entirely avoided. In such cases, the polymers and/or oligomers, might either remain within the reactive monomer product stream, which might than have an insufficient purity, or they might be recycled and enriched within the process and apparatus of the invention, which would at the end cause fouling and unplanned shut downs. To avoid these problems it is preferred to have a device to separate oligomers and/or polymers from a process stream and to withdraw them from the apparatus respectively from the process of the invention. This ensures much longer intervals between plant shut downs and minimizes fouling effects.

In FIGS. 2a, 2b, 4a and 4c to 4e preferred set-ups, all with only one PSU are shown. In FIGS. 2a, 4a, 4c and 4d the polymers and/or oligomers are separated up-stream of the ISU. In these cases, the PSU produces a polymer/oligomer waste stream as well as a stream comprising most of the reactive monomers and inhibitors from the feed stream of PSU. Said reactive monomer streams are named "RM stream 1a" in FIGS. 2a and 4a and is named "RM streams 2a" in FIGS. 4c and 4d. Use of PSUs leads to longer intervals between shut-downs, increases the efficiency of the ISU and reduces costs for the ISU because a smaller volume has to be processed by the ISU and thus smaller membrane dimensions are possible. This at the end saves costs and increases productivity.

Figure 1:
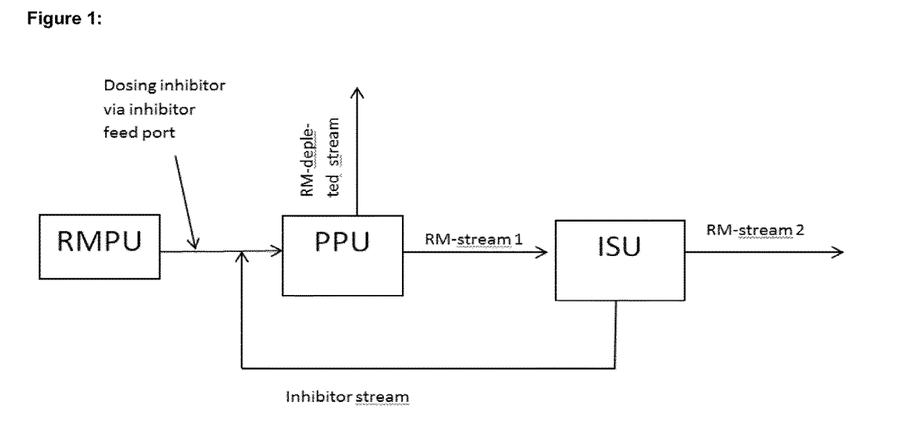
FIG. 1: Apparatus and process for production of reactive monomers with inhibitor recycling (Inhibitor feed port not shown in the Figure).
Figure 2A:
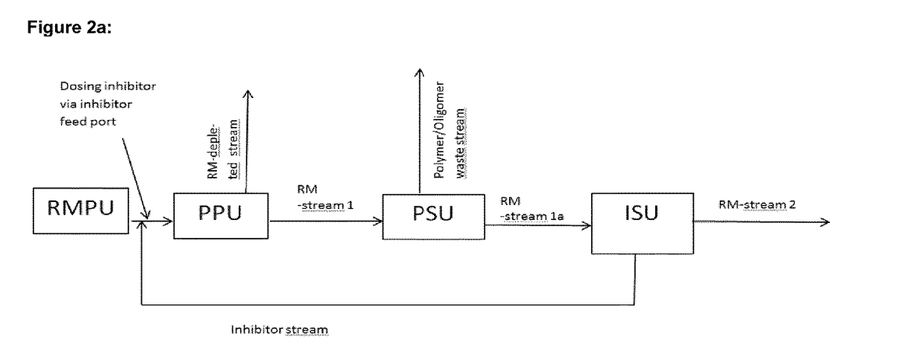
FIG. 2a: Apparatus and process for production of reactive monomers with inhibitor recycling. A polymer separation unit, which allows to separate and withdraw polymers and/or oligomers from the apparatus/process, is arranged upstream of the inhibitor separation unit. (Inhibitor feed port not shown in the Figure).
Figure 2B:
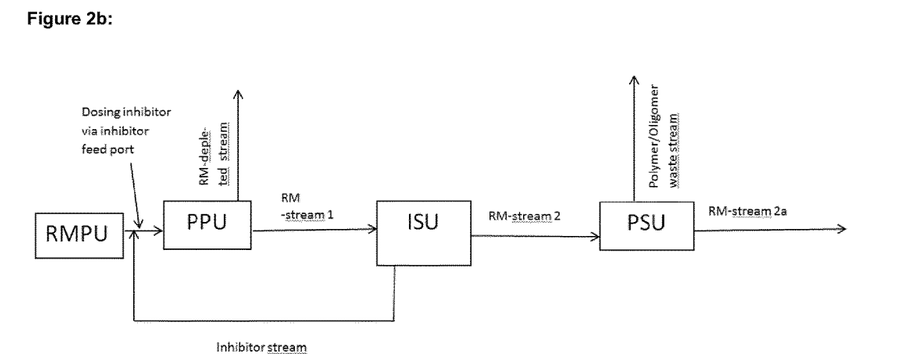
FIG. 2b: Apparatus and process for production of reactive monomers with Inhibitor recycling and, compared to FIG. 2a alternative arrangement, of the polymer separation unit which allows to separate and withdraw polymers and/or oligomers from the apparatus from RM stream 2 (Inhibitor feed port not shown in the Figure).
Figure 4A:
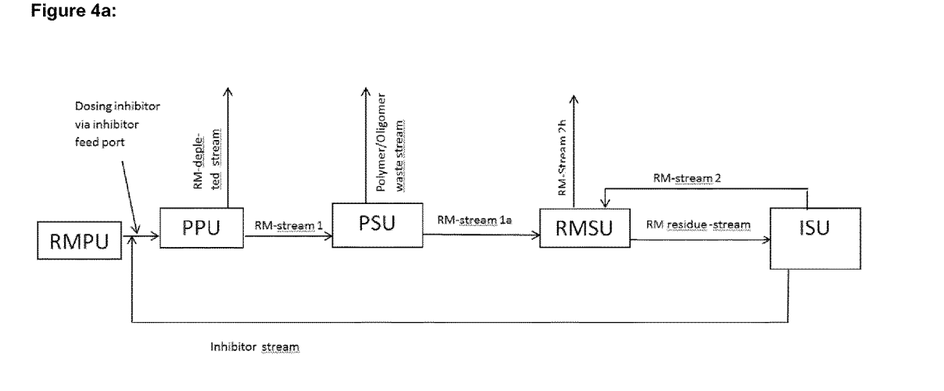
FIG. 4a: Apparatus and process for production of reactive monomers with inhibitor recycling. A primary purification unit, a polymer separation unit and a reactive monomer separation unit are arranged upstream of the inhibitor separation unit (Inhibitor feed port not shown in the Figure).
Figure 4B:
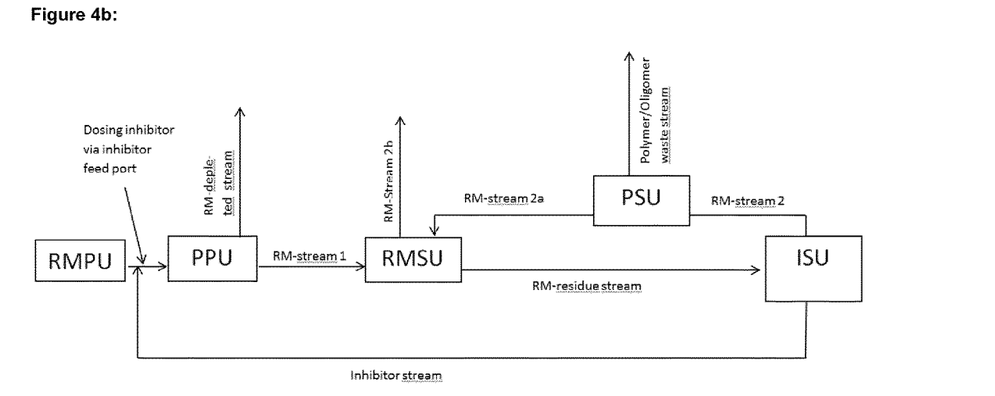
FIG. 4b: Apparatus and process for production of reactive monomers with inhibitor recycling. A primary purification unit and a reactive monomer separation unit are arranged upstream and a polymer separation unit downstream of the inhibitor separation unit (Inhibitor feed port not shown in the Figure).

In FIGS. 2b and 4b the polymers and/or oligomers are separated from RM stream 2, i.e. the PSU is located downstream of the ISU. Said arrangement allows to obtain reactive monomers, free or nearly free of oligomers and/or polymers.

Any device that can be used so separate monomers from oligomers and/or polymers can be used as PSU, preferably distillation devices or membrane separation devices. Such devices are known in the art. Preferably, however, the PSU comprises or consists of at least one distillation device and/or at least one membrane separation unit. In case the PSU is used to separate polymers and/or oligomers from RM stream 1 (see for example FIGS. 2a and 4a), the PSU preferably comprises or consists of at least one distillation device.

In case the PSU is used to separate oligomers and/or polymers form a residue stream of the RMSU (see for example FIG. 4c or 4d or from RM stream 2 (see for example FIG. 2b or 4b) it is preferred, that it comprises at least one distillation device and/or at least one membrane separation unit. Especially preferred it is a membrane separation unit in this case. Most preferred is the apparatus and process according (for example according to FIG. 4c or 4d), wherein the RM residue stream is treated with a two-step membrane separation. The first step is a membrane based PSU and the second step is the ISU. It is preferred to use membrane separation units to separate polymers and oligomers from RM stream 2 or the RM residue stream, because the volume of those streams is low and membrane separation is very effective and energy saving at that stage.

If a membrane separation unit is used as PSU, the membrane preferably has a higher molecular weight cut-off than the membrane used in ISU. The membranes used for the PSU are preferably membranes having a molecular weight cut off from 0.5 to 5 kDa. Membranes with 200 to 500 Da, can be used too even though they might have lower fluxes.

The PSU preferably separates polymers and/or oligomers from small molecules, in particular from reactive monomers and inhibitors.

As indicated before, the PSU is preferably used if formation of polymers and/or oligomers cannot be avoided during the process of the invention. Thus, the apparatus and process of the invention is preferably designed such that the PSU can be switched on and off during operation of the apparatus or process, depending on the polymer and/or oligomer content in a process stream.

In a second special and preferred variant the apparatus and a process of the invention comprise a "reactive monomer separation unit" (RMSU). Said RMSU separates the main amount of reactive monomers from its feed stream. As a consequence, and compared to a process without a RMSU upstream of the ISU, the dimensions of the ISU can be much smaller. This is because the volume to be processed within the ISU is reduced significantly by the RMSU. This on the other hand increases the capacities of the apparatus and reduces costs for the ISU.

The feed stream of the RMSU can be different, depending on the set-up of the apparatus and process of the invention. It is preferred that the feed stream is RM stream 1 or an intermediately modified RM stream 1 (see FIG. 4a). The RMSU produces "RM stream 2b", which is usually withdrawn as product stream from the apparatus and or further processed, and "RM residue stream". Compared to the feed stream of the RMSU RM stream 2b is enriched in reactive monomers and RM residue stream is enriched in inhibitors. RM residue stream usually also comprises a minor amount of reactive monomers. Polymers and/or oligomers might also be comprised therein.

RMSUs are frequently used in conventional purification units for reactive monomers. Thus, suitable devices are well known to a man skilled in the art. Because the RMSU usually has to process high volumes, it preferably comprises at least one distillation device or a crystallization device, most preferably a distillation column.

As indicated in FIGS. 3, 4a, 4c, 4d and 4e, in preferred variants of the apparatus and the process of the present invention the RMSU is directly connected with the PPU unit via RM-stream 1.

Another preferred alternative is shown in FIG. 4a, wherein a PSU is placed between the PPU and the RMSU.

The RM residue stream obtained from the RMSU is preferably forwarded to the ISU (see FIGS. 3, 4a, 4b and 4e) or passed through a PSU (see FIGS. 4c and 4d). Options 4c and 4d and in particular 4e are most preferred.

RM stream 2, obtained from the ISU, may comprise remarkable amounts of reactive monomers. Thus, it is preferred to recycle RM stream 2 directly (see FIGS. 3, 4a and 4c) or via intermediate PSU (see FIG. 4b) to the RMSU. It is however, also preferred to withdraw RM stream 2 from the apparatus and/or process as shown in FIGS. 4d and 4e or further process it before withdrawal.

The apparatus of the present invention is preferably used in a process comprising the following steps:
I. Separating a feed stream comprising reactive monomers within a PPU to obtain "RM-stream 1" and "RM-depleted stream". Definitions see above.
II. Adding at least one inhibitor to a process stream or device used in the process during, before or after step I via at least one inhibitor feed port,
III. Separating RM-stream 1 or a intermediately modified RM-stream 1, into "RM-stream 2" and an "inhibitor stream" within an ISU.

Definitions see above.

The feed stream comprising reactive monomers for PPU the can be obtained as described above from a RMPU.

The process of the invention is characterized in that the inhibitor stream is recycled to at least one inhibitor feed port and that a membrane separation unit is used as ISU.

In step II at least one inhibitor or a mixture of fresh inhibitor and at least a part or all of the recycled inhibitor stream is added to a device comprising reactive monomers and used within the process or into a process stream comprising reactive monomers, during, before or after step I. Preferably, fresh inhibitor or recycled inhibitor can be fed through at least one inhibitor feed port located at a device, like the PPU, PSU or RMSU and/or at a process stream, like the feed stream of the PPU or RM stream 1 or RM stream 1a or RM stream 2a. Preferably at least a part of the fresh or recycled inhibitor is fed through at least one inhibitor feed port located at or upstream of the PPU. Especially preferred is that the main amount or all of the fresh inhibitor is fed through at least one inhibitor feed port located at or upstream of, the PPU, most preferred between the RMPU and PPU.

It is preferred that at least a part of the inhibitor stream is recycled to a feed port upstream of process step I. It is, however, also possible, to recycle the whole or parts of the inhibitor stream to a feed port in process stages IV or V defined below.

The inhibitors respectively the inhibitor stream can be fed to one of the process streams or fed to one of the separating or manufacturing devices of the apparatus of the invention.

If more than one inhibitor is used, then they can be added simultaneously or individually via the same or different ports. It is also possible to feed the whole amount of inhibitor at once or to split it off. Preferably fresh inhibitors are added continuously.

As indicated above when describing the apparatus of the invention, it is preferred to conduct step III directly after step I.

In special but also preferred variants of the present invention a step IV, wherein oligomers and/or polymers are separated from the process streams within a PSU is conducted.

In another special and preferred variant, the process of the invention comprises a step V, wherein the main amount of reactive monomers is separated from the process stream with a RMSU.

Combinations of these process steps alternatives are also possible. The following sequences of steps are preferred for the present invention:
  i. II, I, III (see FIG. 1)
  ii. II, I, III, IV (see FIG. 2b)
  iii. II, I, IV, III (see FIG. 2a)
  iv. II, I, V, III (see FIGS. 3 and 4e)
  v. II, I, IV, V, III (see FIG. 4a)
  vi. II, I, V, IV, III (see FIGS. 4c and 4d)
  vii. II, I, V, III, IV (see FIG. 4b)

Alternative combinations of the process steps I to V not shown in the Figures are possible and are also part of the present invention.

In the preferred options i. to iii. RM stream 2, with or without separation of oligomers and/or polymers, represents the main product stream. These alternatives are especially suitable for small volume applications, otherwise large membrane areas are necessary.

In options iv. to vii. the RM stream 2b, obtained from the RMSU, is the main product stream. In these cases the ISU unit is always used to work-up a residue stream of the RMSU and to split it off into an initiator stream which is recycled to an initiator feed port and into RM-stream 2 which is preferably recycled to the RMSU, directly or via intermediate treating steps like polymer and/or oligomer separation. Alternatively, but not shown in the Figures, RM stream 2 might be recycled to another device or stream, up-stream of the RMSU, or as also preferred it might be withdrawn from the process respectively apparatus (see FIGS. 4d and 4e) or further processed.

Most preferred options are iv to vii.

Further details discussed for the apparatus above are valid for the process of the invention, too.

It is preferred that the concentration of inhibitors is set during step II. to 1-100000 parts per million by weight. The concentration is a result of the addition of fresh inhibitors and the recycling of the inhibitor stream.

In a special variant of the process of the present invention, inhibitors are added during, before or after step I in step II in a manner that ensures, that together with the recycle stream of inhibitor an excess of inhibitor is present in the process streams and/or devices comprising reactive monomer during the process. "Excess" means, that at least 1%, preferably 5 to 99%, more preferred 10 to 80%, even more preferred 20 to 70%, most preferred 40 to 60% and particular preferred about 50% of the inhibitor freshly added in step II are found in the inhibitor stream after the first passage of the ISU. This embodiment has the benefit, that that polymerization can be absolutely minimized and is lower compared to state of the art processes using less amounts of initiators. The process of the invention, however, has comparable or lower costs, because the unreacted initiators are recycled.

Preferred inhibitors used in the process of the present invention are one or more selected from the group consisting of hydroxylamines, oximes, sterically hindered stable nitroxyl radicals, quinone methide inhibitors, nitroaromatics, nitrosoaromatics, benzoquinones, hydroquinones, phenothiazines, phenolic antioxidants, N,N'-dialkyl-p-phenylene diamines, N,N'-dialkyl-p-benzoquinone diimides; more preferably selected from the group consisting of hydroxylamines, sterically hindered stable nitroxyl radicals, quinone methide inhibitors, nitroaromatics, nitrosoaromatics, benzoquinones, hydroquinones, phenothiazines, phenolic antioxidants, N,N'-dialkyl-p-phenylene diamines, N,N'-dialkyl-p-benzoquinone diimides. Particularly preferred inhibitors are selected from the group consisting of quinone methide inhibitors, sterically hindered stable nitroxyl radicals, nitroaromatics.

Hydroxylamines are e.g. described in U.S. Pat. No. 5,282,957. Particularly suitable hydroxylamines have the following general structure (I) or (II):

where x, y are each independently 1 or 2;
a, b are independently selected from 0, 1, 2, 3, 4, 5, 6, 7, 8, 9, 10; preferably a, b are independently selected from 1, 2, 3, 4, 5, 6, 7, 8, 9, 10;
and wherein diethyl hydroxylamine is a even more preferably hydroxylamine.

Quinone methide inhibitors are described e.g. in U.S. Pat. Nos. 4,003,800, 4,040,911, EP 0 737 659, EP 0 737 660, WO 99/48896, US 2005/0027150, EP 2 055 691 A1.

In particular, a first group of quinone methide inhibitors useful in the present invention can be described by the following structure (III):

where $R^1$, $R^2$ are independently selected from the group consisting of hydrogen, alkyl having 1 to 15 carbon atoms;

where $R^3$, $R^4$ are independently selected from the group consisting of
hydrogen;
—CN;
—COOR$^5$;
—COR$^6$;
—OCOR$^7$;
—CONR$^8$R$^9$;
—PO(OR$^{10}$)$_2$;
alkyl having 1 to 15 carbon atoms;
cycloalkyl having 3 to 15 carbon atoms;
an optionally alkyl-substituted aryl having 6 to 12 carbon atoms;
heteroaryl having 2 to 10 carbon atoms;
where $R^5$, $R^6$, $R^7$, $R^8$, $R^9$, $R^{10}$ are selected from the group consisting of hydrogen, alkyl having 1 to 15 carbon atoms, cycloalkyl having 1 to 12 carbon atoms, aryl having 6 to 12 carbon atoms.

One specifically preferred example of the first group of quinone methide inhibitors is a compound according to structure (III) in which $R^1=R^2=$tert-Butyl, $R^3=$H and $R^4=$phenyl.

Moreover, a second group of quinone methide inhibitors useful in the present invention can be described by the following structure (IV):

(IV)

where
$R^{11}$ is selected from the group consisting of —F, —Cl, —Br, —I, —O—R$^{14}$, —S—R$^{15}$;
$R^{12}$, $R^{13}$, $R^{14}$, $R^{15}$ are independently selected from the group consisting of hydrogen, alkyl having 1 to 15 carbon atoms, cycloalkyl having 1 to 15 carbon atoms, aryl having 6 to 12 carbon atoms.

In a preferred embodiment, $R^{11}$=—O—R$^{14}$, wherein $R^{14}$ is alkyl having 1 to 6, preferably 1 to 3 carbon atoms, even more preferably $R^{14}$ is selected from the group consisting of propyl, methyl; and $R^{12}$, $R^{13}$ are independently selected from the group consisting of methyl, tert-butyl, preferably tert-butyl.

Sterically hindered stable nitroxyl radicals that are particularly useful are described e.g. in EP 2 055 691 A1 and U.S. Pat. No. 5,254,760.

In particular, sterically hindered nitroxyl radicals useful in the present invention can be described by the following structures (V), (VI), (VII), (VIII):

(V)

(VI)

(VII)

(VIII)

where
$R^{16}$, $R^{17}$, $R^{18}$, $R^{19}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ are each independently alkyl having 1 to 4 carbon atoms;
$R^{20}$, $R^{21}$ are each independently selected from the group consisting of
hydrogen;
alkyl having 1 to 20 carbon atoms;
—NR$^{38}$R$^{39}$; —F; —Cl; —Br; —I; —OR$^{40}$; —COOR$^{41}$; —O—CO—NHR$^{42}$; —NH—CO—R$^{43}$; —O—CO—R$^{44}$;
where $R^{38}$, $R^{39}$, $R^{40}$, $R^{41}$, $R^{42}$, $R^{43}$, $R^{44}$ are each independently selected from hydrogen;
alkyl having 1 to 20 carbon atoms;
aryl having 1 to 12 carbon atoms, wherein one or more hydrogens are each optionally substituted by alkyl having 1 to 6 carbon atoms;
benzyl, wherein one or more hydrogens are each optionally substituted by alkyl having 1 to 4 carbon atoms;
and where c is 1, 2, 3, 4, 5, or 6;
E is a bivalent residue selected from the group consisting of alkylene with 1 to 20 carbon atoms, arylene with 6 to 12 carbon atoms, alkarylene with 6 to 20 carbon atoms, aralkylene with 6 to 20 carbon atoms,
that can each optionally contain hetero atoms such as O, S, N and that can each optionally contain carbonyl groups.

In addition, the sterically hindered nitroxyl radical useful in the present invention can also be selected from the group consisting of
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-S-triazine, and 4,4'-ethylenebis(1-oxyl-2,2,6,6-tetramethylpiperazin-3-one).

In an even more preferred embodiment, $R^{16}$, $R^{17}$, $R^{18}$, $R^{19}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ are each methyl; $R^{20}$ is hydrogen, while all the other residues are as defined above.

Especially preferred sterically hindered nitroxyl radicals are selected from
2,2,6,6-tetramethylpiperidine-N-oxyl (TEMPO);
4-acetamido-2,2,6,6-tetramethylpiperidine-N-oxyl (AA-TEMPO);
4-hydroxy-2,2,6,6-tetramethylpiperidine-N-oxyl (4-hydroxy-TEMPO);
4-oxo-2,2,6,6-tetramethylpiperidine-N-oxyl (oxo-TEMPO);
1-oxyl-2,2,6,6-tetramethylpiperidin-4-yl acetate;
1-oxyl-2,2,6,6-tetramethylpiperidin-4-yl-2-ethylhexanoate;
1-oxyl-2,2,6,6-tetramethylpiperidin-4-yl stearate;
1-oxyl-2,2,6,6-tetramethylpiperidin-4-yl benzoate;
1-oxyl-2,2,6,6-tetramethylpiperidin-4-yl 4-tert-butylbenzoate;
a compound of the structure (VI) where $R^{22}=R^{23}=R^{24}=R^{25}=$methyl, $R^{20}=$hydrogen, $R^{21}=-OR^{40}$, where $R^{40}=$alkyl having 1 to 6, or even 1 to 4, carbon atoms; where 4-butoxy-2,2,6,6-tetramethylpiperidine-N-oxyl (4-butoxy-TEMPO) is to be specifically mentioned;
a compound of the structure (VII) where $R^{26}=R^{27}=R^{28}=R^{29}=$methyl and c=2;
bis(1-oxyl-2,2,6,6-tetramethylpiperidin-4-yl) succinate,
bis(1-oxyl-2,2,6,6-tetramethylpiperidin-4-yl) adipate,
bis(1-oxyl-2,2,6,6-tetramethylpiperidin-4-yl) sebacate,
bis(1-oxyl-2,2,6,6-tetramethylpiperidin-4-yl) n-butylmalonate,
bis(1-oxyl-2,2,6,6-tetramethylpiperidin-4-yl) phthalate,
bis(1-oxyl-2,2,6,6-tetramethylpiperidin-4-yl) isophthalate,
bis(1-oxyl-2,2,6,6-tetramethylpiperidin-4-yl) terephthalate,
bis(1-oxyl-2,2,6,6-tetramethylpiperidin-4-yl) hexahydroterephthalate,
N,N'-bis(1-oxyl-2,2,6,6-tetramethylpiperidin-4-yl)adipamide,
N-(1-oxyl-2,2,6,6-tetramethylpiperidin-4-yl)-caprolactam,
N-(1-oxyl-2,2,6,6-tetramethylpiperidin-4-yl)-dodecylsuccinimide,
2,4,6-tris-[N-butyl-N-(1-oxyl-2,2,6,6-tetramethylpiperidin-4-yl]-s-triazine, and
4,4'-ethylenebis(1-oxyl-2,2,6,6-tetramethylpiperazin-3-one).

Of these especially preferred sterically hindered nitroxyl radicals, the following are the most preferred:
2,2,6,6-tetramethylpiperidine-N-oxyl (TEMPO);
4-acetamido-2,2,6,6-tetramethylpiperidine-N-oxyl (AA-TEMPO);
4-hydroxy-2,2,6,6-tetramethylpiperidine-N-oxyl (4-hydroxy-TEMPO);
4-butoxy-2,2,6,6-tetramethylpiperidine-N-oxyl (4-butoxy-TEMPO);
4-oxo-2,2,6,6-tetramethylpiperidine-N-oxyl (oxo-TEMPO).

Nitroaromatics especially useful for the present invention are for example described in U.S. Pat. No. 5,254,760. Nitroaromatics that are preferably used according to the invention are selected from the group consisting of 1,3-dinitrobenzene, 1,4-dinitrobenzene, 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrochlorobenzene, 2,4-dinitrophenol, 2,4-dinitro-6-sec-butylphenol, 4-cyano-2-nitrophenol, and 3-iodo-4-cyano-5-nitrophenol. Even more preferable nitroaromatics are 2,4-dinitro-6-sec-butylphenol (DNBP), 2,4-dinitrophenol (DNP), 4,6-dinitro-ortho-cresol (DNOC), with 2,4-dinitro-6-sec-butylphenol (DNBP) being the most preferred nitroaromatic. As stated before, 2,4-dinitro-6-sec-butylphenol (DNBP) is an inhibitor which belongs to the inhibitor subclass of retarders.

Nitrosoaromatics useful for the present invention are for example described in EP 1 474 377 B1 and can specifically be selected from the group consisting of nitrosophenol compounds, nitrosoaniline compounds.

Preferred nitrosophenol compounds are selected from the group consisting of 4-nitrosophenol, 2-nitrosophenol, 4-nitroso-o-cresol, 2-nitroso-p-cresol, 2-tert-butyl-4-nitrosophenol, 4-tert-butyl-2-nitrosophenol, 2,6-di-tert-butyl-4-nitrosophenol, 2-tert-amyl-4-nitrosophenol, 4-tert-amyl-2-nitrosophenol, 2,6-di-tert-amyl-4-nitrosophenol, 2-nitroso-1-naphthol, 4-nitroso-1-naphthol, 2-tert-butyl-4-nitroso-1-naphthol, 1-nitroso-2-naphthol, 6-nitroso-2-naphthol, 2-tert-amylnitroso-1-naphthol.

Preferred nitrosoaniline compounds are selected from the group consisting of 4-nitroso-N-(1,4-dimethylpentyl)aniline, 4-nitroso-N-phenylaniline, 4-nitroso-N-isopropylaniline, 4-nitroso-N,N-dimethylaniline, 4-nitroso-N,N-diethylaniline, 4-nitroso-N,N-diphenylaniline, 4-nitroso-N,N-diisopropylaniline, 4-nitrosoaniline, 2-nitroso-N-(1,4-dimethylpentyl)aniline, 2-nitroso-N-phenylaniline, 2-nitroso-N,N-dimethylaniline, 2-nitroso-N,N-diethylaniline, 2-nitroso-N,N-diphenylaniline, 2-nitrosoaniline, 2-tert-butyl-4-nitroso-N-(1,4-dimethylpentyl)aniline, 2-methyl-4-nitroso-N-(1,4-dimethylpentyl)aniline, 2-tert-butyl-4-nitroso-N-phenylaniline, 2-methyl-4-nitroso-N-phenylaniline, 4-tert-butyl-2-nitroso-N-(1,4-dimethylpentyl)aniline, 4-tert-butyl-2-nitroso-N-phenylaniline, 4-tert-butyl-2-nitroso-N,N-dimethylaniline, 4-tert-butyl-2-nitroso-N,N-diethylaniline, 4-tert-butyl-2-nitroso-N,N-diphenylaniline, 4-nitroso-N-(1,3-dimethylbutyl)aniline, 2-nitroso-N-(1,3-dimethylbutyl)aniline, 4-tert-butyl-2-nitrosoaniline.

Hydroquinones useful in the present invention can be described by the following structure (IX), and benzoquinones useful in the present invention can be described by the following structure (X):

(IX)

(X)

where
$R^{45}$, $R^{46}$, $R^{47}$, $R^{48}$, $R^{49}$, $R^{50}$, $R^{51}$, $R^{52}$ are independently selected from the group consisting of hydrogen;
alkyl having 1 to 20 carbon atoms;
—F; —Cl; —Br; —I; —OR$^{53}$; where R$^{53}$ is selected from hydrogen, alkyl having 1 to 20 carbon atoms or aryl having 1 to 12 carbon atoms;

where the two residues $R^{45}$ and $R^{46}$ can also form an aromatic or aliphatic cycle with each other, where the two residues $R^{47}$ and $R^{48}$ can also form an aromatic or aliphatic cycle with each other, where the two residues $R^{49}$ and $R^{50}$ can also form an aromatic or aliphatic cycle with each other, where the two residues $R^{51}$ and $R^{52}$ can also form an aromatic or aliphatic cycle with each other.

Preferred hydroquinones according to the present invention are those of formula (IX) in which one of $R^{45}$, $R^{46}$, $R^{47}$, $R^{48}$ is alkyl having 1 to 20, preferably 1 to 6 carbon atoms, more preferred tert-butyl or methyl, even more preferred methyl, and the other three residues of $R^{45}$, $R^{46}$, $R^{47}$, $R^{48}$ are each hydrogen.

Alternatively, preferred hydroquinones according to the present invention are those of formula (IX) in which two of $R^{45}$, $R^{46}$, $R^{47}$, $R^{48}$ are each alkyl having 1 to 20, preferably 1 to 6 carbon atoms, more preferred tert-butyl or methyl, even more preferred methyl, and the other two residues of $R^{45}$, $R^{46}$, $R^{47}$, $R^{48}$ are each hydrogen.

In another preferred embodiment, $R^{45}=R^{46}=R^{47}=R^{48}=H$ in formula (IX).

Preferred benzoquinones according to the present invention are those of formula (X) in which one of $R^{49}$, $R^{50}$, $R^{51}$, $R^{52}$ is alkyl having 1 to 20, preferably 1 to 6 carbon atoms, more preferred tert-butyl or methyl, even more preferred methyl, and the other three residues of $R^{49}$, $R^{50}$, $R^{51}$, $R^{52}$ are each hydrogen.

Alternatively, preferred hydroquinones according to the present invention are those of formula (X) in which two of $R^{49}$, $R^{50}$, $R^{51}$, $R^{52}$ are each alkyl having 1 to 20, preferably 1 to 6 carbon atoms, more preferred tert-butyl or methyl, even more preferred methyl, and the other two residues of $R^{49}$, $R^{50}$, $R^{51}$, $R^{52}$ are each hydrogen.

In another preferred embodiment, $R^{49}=R^{50}=R^{51}=R^{52}=H$ in formula (X).

Phenothiazines which are particularly useful in the present invention are those which display the structure (XI):

where R*, $R^{54}$, $R^{55}$, $R^{56}$, $R^{57}$, $R^{58}$, $R^{59}$, $R^{60}$, $R^{61}$ are independently selected from the group consisting of hydrogen, alkyl with 1 to 20 carbon atoms.

In a preferred embodiment of structure (XI), R* and one residue of $R^{54}$, $R^{55}$, $R^{56}$, $R^{57}$, $R^{58}$, $R^{59}$, $R^{60}$, $R^{61}$ are independently selected from the group consisting of hydrogen, alkyl with 1 to 20 carbon atoms, while all the other residues are hydrogen.

In a further preferred embodiment, R* and $R^{55}$ are independently selected from the group consisting of hydrogen, alkyl with 1 to 6 carbon atoms, while $R^{54}=R^{56}=R^{57}=R^{58}=R^{59}=R^{60}=R^{61}=H$.

Phenolic antioxidants which are particularly useful in the present invention are those which display the structure (XII):

where $R^{62}$, $R^{63}$, $R^{64}$, $R^{65}$, $R^{66}$ are independently selected from the group consisting of hydrogen, alkyl with 1 to 20 carbon atoms, aryl with 6 to 12 carbon atoms, benzyl group, and where, additionally, each of $R^{62}$, $R^{63}$, $R^{65}$, $R^{66}$ can also be hydroxyl where optionally one or more hydrogen atoms of the aryl group with 6 to 12 carbon atoms or the benzyl group is substituted by a residue selected from the group consisting of hydroxyl, halogen, alkyl with 1 to 6 carbon atoms.

In a preferred embodiment, the residues $R^{62}$, $R^{63}$, $R^{64}$, $R^{65}$, $R^{66}$ in formula (XII) are selected as follows:

$R^{62}$ and $R^{66}$ are each independently selected from the group consisting of hydroxyl, alkyl with 1 to 6 carbon atoms, more preferred from the group consisting of hydroxyl, methyl, tert-butyl;

$R^{64}$ is selected from the group consisting of alkyl with 1 to 6 carbon atoms, benzyl, where optionally one or more hydrogen atoms of the benzyl is substituted by a residue selected from the group consisting of hydroxyl, alkyl with 1 to 6 carbon atoms.

Particularly preferred phenolic antioxidants are those of the following formulas (XII-A), (XII-B), (XII-C) and (XII-D):

(XII-D)

N,N'-dialkyl-p-phenylene diamines that are particularly useful in the present invention are those of the formula (XIII), while N,N'-dialkyl-p-benzoquinone diimides that are particularly useful in the present invention are those of the formula (XIV):

(XIII)

(XIV)

where
$R^{67}$, $R^{68}$, $R^{73}$, $R^{74}$ are each independently alkyl with 1 to 20 carbon atoms;
$R^{69}$, $R^{70}$, $R^{71}$, $R^{72}$, $R^{75}$, $R^{76}$, $R^{77}$, $R^{78}$ are each independently selected from the group consisting of hydrogen; alkyl having 1 to 20 carbon atoms;
—F; —Cl; —Br; —I; —$OR^{79}$; where $R^{79}$ is hydrogen, alkyl having 1 to 20 carbon atoms or aryl having 1 to 12 carbon atoms;
where the two residues $R^{69}$ and $R^{70}$ can also form an aromatic or aliphatic cycle with each other,
where the two residues $R^{71}$ and $R^{72}$ can also form an aromatic or aliphatic cycle with each other,
where the two residues $R^{75}$ and $R^{76}$ can also form an aromatic or aliphatic cycle with each other,
where the two residues $R^{77}$ and $R^{78}$ can also form an aromatic or aliphatic cycle with each other.
In a preferred embodiment of formula (XIII), $R^{69}=R^{70}=R^{71}=R^{72}=H$, while $R^{67}=R^{68}=$alkyl group with 1 to 20 carbon atoms. Even more preferred in formula (XIII), $R^{69}=R^{70}=R^{71}=R^{72}=H$, while $R^{67}=R^{68}=$alkyl group with 1 to 10, or even 1 to 6, carbon atoms.
In a preferred embodiment of formula (XIV), $R^{75}=R^{76}=R^{77}=R^{78}=H$, while $R^{73}=R^{74}=$alkyl group with 1 to 20 carbon atoms. Even more preferred in formula (XIV), $R^{75}=R^{76}=R^{77}=R^{78}=H$, while $R^{73}=R^{74}=$alkyl group with 1 to 10, or even 1 to 6, carbon atoms.
Preferably the membranes used in the PSU are different to those used in the ISU. While both membranes are OSN membranes, the membranes used in the PSU preferably have larger pores and higher flux, while the membranes used in the ISU preferably have smaller pores.

Preferred membranes used in the ISU unit are nanofiltration membranes having a molecular weight cut off from 150 to 900 g/mol, preferably 150 to 500 g/mol.

In case membrane separation is also used within the PSU, membranes used are preferably membranes having a molecular weight cut off from 0.5 to 5 kDa.

The at least one selective membrane according to the present disclosure may be formed from any polymeric or ceramic material which provides a separating layer capable of separating the desired inhibitors or polymeric or oligomeric compound from at least solvent. For example, the at least one selective membrane may be formed from or comprise a material chosen from polymeric materials suitable for fabricating microfiltration, ultrafiltration, nanofiltration, or reverse osmosis membranes, including polyethylene, polypropylene, polytetrafluoroethylene (PTFE), polyvinylidene difluoride (PVDF), polysulfone, polyethersulfone, polyacrylonitrile, polyamide, polyimide, polyamideimide, polyetherimide, cellulose acetate, polyaniline, polypyrrole, polyetheretherketone (PEEK), polybenzimidazole, and mixtures thereof. The at least one selective membrane can be made by any technique known to the art, including sintering, stretching, track etching, template leaching, interfacial polymerization, or phase inversion.

In at least one preferred embodiment, the at least one selective membrane may be crosslinked or treated so as to improve its stability in the process stream. For example, non-limiting mention may be made of the membranes described in GB2437519, the contents of which are incorporated herein by reference.

In at least one preferred embodiment, the at least one selective membrane is a composite material comprising a support and a thin, non-porous, selectively permeable layer. The thin, non-porous, selectively permeable layer may, for example, be formed from or comprise a material chosen from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, crosslinked polyether, polyamide, polyaniline, polypyrrole, and mixtures thereof.

In another preferred embodiment, the at least one selective membrane is prepared from an inorganic material such as, for example, silicon carbide, silicon oxide, zirconium oxide, titanium oxide, and zeolites, using any technique known to those skilled in the art such as sintering, leaching, or sol-gel processing.

In a further preferred embodiment, the at least one selective membrane comprises a polymer membrane with dispersed organic or inorganic matrices in the form of powdered solids present at amounts up to 20 wt % of the polymer membrane. Carbon molecular sieve matrices can be prepared by pyrolysis of any suitable material as described in U.S. Pat. No. 6,585,802. Zeolites as described in U.S. Pat. No. 6,755,900 may also be used as an inorganic matrix. Metal oxides, for example, titanium dioxide, zinc oxide, and silicon dioxide may be used, such as the materials available from Evonik Industries AG (Germany) under their AEROSIL and ADNANO trademarks. Mixed metal oxides such as mixtures of cerium, zirconium, and magnesium oxides may also be used. In at least one embodiment, the matrices will be particles less than about 1.0 micron in diameter, for example less than about 0.1 microns in diameter, such as less than about 0.01 microns in diameter.

In at least one embodiment, the at least one selective membrane comprises two membranes. In another embodiment, the at least one selective membrane comprises three membranes.

Most preferably organic solvent nanofiltration membranes of the phase inversion type (e.g. produced from polyimide dope solutions) or rubber-coated type (e.g. coated with rubber compounds such as silicone and derivatives) or thin-film composite type (e.g. with a separating layer generated via interfacial polymerisation) are used in this invention.

Particularly preferred membranes of the present invention are polyimide membranes, particularly preferred made of P84 (CAS No. 9046-51-9) and P84HT (CAS No. 134119-41-8) and/or blends thereof and/or blends comprising one or both of said polyimides. In preferred embodiments the polyimide membranes are be crosslinked according to GB2437519. To avoid lengthy text repetitions the content of GB 2437519 is herewith incorporated by reference to the description of present application as a whole. Also particular preferred in the present invention are organic coated polyimide membranes, particularly preferred made of above mentioned crosslinked or non-crosslinked P84 and/or P84HT membranes. Very good results have been achieved with crosslinked or non-crosslinked, coated polyimide membranes, especially made of P84 and/P84HT and/or mixtures thereof, wherein the coating comprises silicone acrylates. Particular preferred silicone acrylates to coat the membranes are described in U.S. Pat. Nos. 6,368,382, 5,733,663, JP 62-136212, P 59-225705, DE 102009047351 and in EP 1741481 A1. To avoid lengthy repetitions the contents of both patent applications are incorporated by reference to the present application. They are part of the description and in particular of the claims of the present invention. Most preferred are combination of the especially preferred polyimides mentioned above with the silicone acrylates claimed in DE 102009047351 and in EP 1741481 A1. These combinations are part of the claim of the present invention.

For polar aprotic solvents, polar solvents and water/solvent mixtures membranes according to GB2437519 are most preferred. Such membranes are available under the trademark DuraMem® from Evonik Membrane Extraction Technology, UK. For more non-polar solvents and non-polar solvents PuraMem® 280 and the silicone acrylate modified membranes according to DE102009047351 and EP 1741481 A1, in particular made of made of P84 (CAS No. 9046-51-9) and P84HT (CAS No. 134119-41-8) or blends thereof or blends comprising one or both of said polyimides, are especially preferred.

The examples presented below are intended for better understanding of the invention. They do not at all limit the scope of the present invention.

EXAMPLE 1: MEMBRANE SCREENING—INHIBITOR/RETARDER SEPARATION

In the inventive method, it is possible to apply the organic solvent nanofiltration (OSN) membranes at several points within the reactive monomer production process, for example in the ISU or in the PSU. Several membranes of different types, as well as a number of inhibitor compounds were selected in order to obtain an overview of which combinations may provide the best values of rejection and flux for a viable process.

For the purposes of this screening test, toluene was selected as the solvent system to provide a "mimic" of styrene due to handling and potential polymerisation issues when using styrene in the general-purpose (i.e. not specifically designed for handling reactive monomers) nanofiltration equipment.

Five OSN membranes manufactured by Evonik Membrane Extraction Technology (London, UK) were selected for this screening experiment:
  (i) PuraMem™ 280—a polyimide-based homogeneous, asymmetric membrane of nominal molecular weight cut-off of 280 Da;
  (ii) PuraMem™ S600—a composite membrane with a silicone separation layer of nominal molecular weight cut-off of 600 Da;
  (iii) PuraMem™ XP3—a composite membrane with a silicone separation layer of nominal molecular weight cut-off of 350 Da;
  (iv) PuraMem™ XP4—a composite membrane with a silicone separation layer of nominal molecular weight cut-off of 330 Da;
  (v) PuraMem™ XP3—a composite membrane with a silicone separation layer of nominal molecular weight cut-off of <250 Da;

One quinone methide inhibitor mixture (abbreviated as "mixture AB" hereinafter) and one retarder compound ("DNBP") were provided for the trials:
  The quinone methide inhibitor mixture "AB" has the general formula (IV) in which $R^{12}=R^{13}$=tert Butyl; and in which $R^{11}$=—O—$R^{14}$, wherein $R^{14}$ is alkyl as defined above.
  DNBP as a polymerisation retarder (DNBP=2,4-dinitro-6-sec-butylphenol).

The equipment used for the membrane screening experiments was a METcell cross-flow filtration apparatus (Evonik Membrane Extraction Technology Ltd., London, U.K.) as shown schematically in FIG. 5. The METcell crossflow system consisted of an 800 mL capacity feed vessel and a pumped recirculation loop through four to six cross-flow cells connected in series (FIG. 5 shows the system configured for four crossflow cells). Circular samples of the membrane(s) selected for testing were placed in each cross-flow cell. Liquid mixing in the cross-flow cells was generated by flow from the recirculation pump (a gear pump is used for this purpose): The liquid flow enters each crossflow cell tangentially to the membrane surface at the outer diameter of the membrane disk and followed a spiral flow pattern to a discharge point at the centre of the filtration cell/disk. The nanofiltration membrane disks were conditioned with toluene at an applied pressure of 30 bar and system temperature of 30° C. until a constant flux was obtained, to ensure that any preservatives/conditioning agents were washed out of the membrane, and maximum compaction of the membrane was obtained. The applied filtration pressure was provided from a high-pressure supply of nitrogen gas.

Once the conditioning process was complete, the system was drained and the toluene replaced with the inhibitor test solution. 4000 ppm (v/v) of each inhibitor composition was added to toluene to generate the test solutions. Care was taken not to allow the membranes to dry during the draining process.

The inhibitor test mixture was then permeated across each conditioned membrane disk at an applied pressure of 30 bar and system temperature of 30° C. for 4 hours. The liquid permeating the membranes was collected and pumped back into the feed vessel using a HPLC pump. This maintains a constant volume and constant sample concentration within the filtration equipment. Samples of feed permeate and retentate solutions were collected for analysis.

Inhibitor concentration was measured using gas chromatography. The method was as follows:
- a. Capillary gas chromatograph with FID detector (e.g. Agilent 6850 or equivalent)
- b. Column—Agilent HP-5 (30 m long, ×0.25 mm diameter×0.25 micron film thickness) or equivalent
- c. Column temperature programme
  100° C. for 10 minutes
  Ramp at 10° C./min to 180° C.
  Hold at 180° C. for 10 minutes
- d. Injector temperature—250° C.
- e. Detector temperature—300° C.
- f. Carried gas—helium, 1 mL/min
- g. Injection volume—1 μL Retention time of the inhibitor compounds was confirmed using standards of the individual components.

Two screening experiments were performed. In the first test, see Table 1, DNBP was tested. Mixture "AB" was tested in a separate experiment, see Table 2.

TABLE 1

Feed solution 1 (DNBP) - membranes performance results

| Membrane | Flux | DNBP |
|---|---|---|
| PM 280 | 60 LMH | 66% |
| PMS 600 | 76 LMH | 42% |
| XP3 | 138 LMH | 44% |
| XP4 | 107 LMH | 48% |
| XP5 | 11.5 LMH | 69% |

TABLE 2

Feed solution 2 ("AB") - membranes performance results

| | | Rejection of "AB" | |
|---|---|---|---|
| Membrane | Flux | Compound A* | Compound B* |
| PM 280 | 85 LMH | 86% | 93% |
| PMS 600 | 73 LMH | 52% | 58% |
| XP3 | 100 LMH | 60% | 66% |
| XP4 | 82 LMH | 58% | 65% |
| XP5 | 8.6 LMH | 80% | 85% |

Two peaks are present in the chromatogram for "AB", and both were individually quantified.

The data in Tables 1 and 2 indicates the following:
- The inhibitor formulation "AB" is the best rejected composition with all of the tested membranes;
- The PM280 membrane showed the best overall performance (looking at both flux and rejection) for inhibitor recovery; the rejection of "AB" is as high as 93% with PM280.
- The retarder formulation DNBP shows a rejection of 66% with PM280, indicating that is recoverable by OSN
- The rejection of inhibitors increases as the molecular weight cut-off decreases for the series of XP membranes

EXAMPLE 2: MEMBRANE SCREENING—OLIGOMER AND POLYMERIC STYRENE

In some embodiments of the inventive process, in addition to separating inhibitor from monomer in an ISU, it may also be advantageous to remove oligomeric or polymeric species from the monomer/inhibitor system within a PSU prior to separating inhibitor from monomer. This would allow OSN membranes to be used in process configurations that either replace or debottleneck a conventional "tar still" (i.e. a distillation column used in conventional approaches to remove the high-boiling residual oligomeric/polymeric species).

By way of a representative example, oligomeric stryrene was selected as it is readily available from companies such as Agilent and can be analysed via HPLC or GPC techniques. Standards of average molecular weight 580 g/mol and 1,000 g/mol from Agilent were used in these tests (part numbers PL2012-2001 and PL2012-3001).

PuraMem™ S600 and PuraMem™280 were selected for evaluation with oligomeric styrene as on average they offered the highest and lowest rejection values of all membranes tested in Example 1 (see Tables 1 and 2).

The experimental protocol was the same as Example 1, except that the test solution consisted 1 g/L of a-methylstyrene dimer (Sigma-Aldrich, UK) and 2 g/L of each styrene oligomer standard dissolved in toluene. The concentration of each styrene oligomer was determined using the HPLC method described in See Toh et al, (Journal of Membrane Science, 291(1-2) (2007), 120-125).

The curves of rejection versus molecular weight for PM280 and PM S600 are shown in FIG. 6. It can been clearly seen that for both membranes high rejections are achieved at molecular weights above 700 g/mol.

The ideal membrane for oligomer/polymer rejection in a PSU would have high (>90%) rejection of oligomeric/polymeric species, and low rejection of inhibitor. Based on this criteria, PM S600 is viable for this separation in a PSU.

The examples together with the information provided in the description allow a person skilled in the art to adjust the process to other sequences of unit operations and other reactive monomers.

DESCRIPTION OF THE FIGURES

FIG. 4c: Apparatus and process for production of reactive monomers with inhibitor recycling. A reactive monomer purification unit and a polymer separation unit are arranged downstream of the primary purification unit and upstream of the inhibitor separation unit (Inhibitor feed port not shown in the Figure). RM stream 2, which might comprise reactive monomers, is recycled to the RMSU. Polymers and oligomers are withdrawn via the polymer/oligomer waste stream.

FIG. 4d: Apparatus and process for production of reactive monomers with inhibitor recycling. A reactive monomer separation unit and a polymer separation unit are arranged downstream of the primary purification unit and upstream of the inhibitor separation unit. The inhibitor stream is recycled and RM stream 2 withdrawn or further processed. Preferably PPU and/or RMSU are distillation devices in this embodiment (Inhibitor feed port not shown in the Figure).

FIG. 4e: Apparatus and process for production of reactive monomers with inhibitor separation unit arranged downstream of the reactive monomer separation unit. The inhibitor stream is recycled and RM stream 2 withdrawn or further processed. Preferably PPU and/or RMSU are distillation devices in this embodiment (Inhibitor feed port not shown in the Figure).

FIG. 5: Cross Flow filtration apparatus as used in the examples.

FIG. 6: Results of Example 2.

The invention claimed is:

1. An apparatus for the production of reactive monomers, comprising:
   a) at least one inhibitor feed port;
   b) a primary purification unit "PPU", separating a feed stream comprising reactive monomers into "RM-stream 1", enriched in reactive monomers and "RM-depleted stream," depleted in reactive monomers, wherein "enriched" means that the concentration of the reactive monomers in RM-stream 1 is higher than in the feed stream of the PPU and "depleted" means, that the concentration of the reactive monomers in the RM-depleted stream is lower than in the feed stream of the PPU;
   c) an inhibitor separation unit "ISU", separating RM-stream 1, or an intermediate modified RM-stream 1, into "RM-stream 2", enriched in the reactive monomers, and an "inhibitor stream," enriched in inhibitors and depleted in reactive monomers, wherein "enriched" means that the concentration of reactive monomers in RM stream 2 is higher than in the feed stream of the ISU and that the concentration of inhibitors in the inhibitor stream is higher than in the feed stream of the ISU;
   and wherein the apparatus is designed such that the inhibitor stream is recycled to at least one inhibitor feed port, and the ISU is a membrane separation unit comprising OSN nanofiltration membranes having a molecular weight cut off from 150 to 900 g/mol.

2. The apparatus of claim 1, further comprising a polymer separation unit "PSU," producing a "polymer/oligomer waste stream", and a second stream, depleted in polymers and/or oligomers compared to the feed stream of the PSU.

3. The apparatus of claim 2, wherein the PSU is a membrane separation unit, comprising membranes with a molecular weight cut off from 500 to 1000 Da or of from 1 to 5 kDa.

4. The apparatus of claim 2, wherein:
   a) the polymer/oligomer waste stream can be withdrawn from the apparatus; and/or
   b) the PSU can be switched on and off during operation of the apparatus.

5. The apparatus of claim 1, further comprising a reactive monomer separation unit "RMSU", which separates the main amount of reactive monomers from the feed stream of the RMSU to produce "RM stream 2b" and which, in addition, produces an "RM residue stream," which is depleted in reactive monomers compared to the feed stream of the RMSU.

6. The apparatus of claim 5, further comprising a polymer separation unit "PSU," producing a "polymer/oligomer waste stream", and a second stream, depleted in polymers and/or oligomers compared to the feed stream of the PSU and wherein the PSU is a membrane separation unit comprising membranes with a molecular weight cut off from 500 to 1000 Da or of from 1 to 5 kDa.

7. The apparatus of claim 5, wherein:
   a) RM stream 1 is fed into the RMSU; or
   b) RM stream 1 is fed to a PSU and the polymer/oligomer depleted stream of the PSU is fed into the RMSU or the ISU.

8. The apparatus of claim 5, wherein:
   a) the RM residue stream is fed into the ISU; or
   b) the RM residue stream is fed to a PSU and that the polymer and/or oligomer depleted stream of the PSU is fed to the ISU.

9. The apparatus of claim 5, wherein:
   a) RM stream 2 is recycled to the RMSU or further processed or withdrawn; or
   b) RM stream 2 is fed to a PSU and the polymer and/or oligomer depleted stream of the PSU is recycled to the RMSU.

10. A process for the production of reactive monomers, comprising the steps:
   I. separating a feed stream comprising reactive monomers within a PPU to obtain RM-stream 1 and an RM-depleted stream;
   II. adding at least one inhibitor to a process stream or device used in the process during, before or after step I via at least one inhibitor feed port;
   III. separating RM-stream 1, or an intermediately modified RM-stream 1, into "RM-stream 2" and an "inhibitor stream" within an ISU; wherein:
      a) the inhibitor stream obtained from the ISU is recycled to at least one inhibitor feed port; and
      b) a membrane separation unit is used as the ISU, comprising OSN nanofiltration membranes having a molecular weight cut off from 150 to 900 g/mol.

11. The process of claim 10, further comprising:
   IV. separating oligomers and/or polymers from the process with a PSU to produce a "polymer/oligomer waste stream", and a second stream, depleted in polymers and/or oligomers compared to the feed stream of the PSU; and/or
   V. separating reactive monomers from the process with a RMSU.

12. The process of claim 11, wherein the PSU is a membrane separation unit comprising membranes with a molecular weight cut off from 500 to 1000 Da or of from 1 to 5 kDa.

13. The process of claim 11, wherein:
a) the polymers and/or oligomers separated with the PSU are withdrawn from the apparatus; and/or
b) that the PSU is switched on or off during operation of the apparatus, if the polymer and/or oligomer content in at least one process stream or device exceeds a specified value.

14. The process of claim 11, wherein process steps are carried out in one of the following sequences:
a) II, I, III;
b) II, I, III, IV;
c) II, I, IV, III;
e) II, I, IV, V, III;
f) II, I, V, IV, III; or
g) II, I, V, III, IV.

15. The process of claim 14, wherein the inhibitors are added during step II and reach a concentration in a process stream upstream of the ISU of from 1-100000 parts per million.

16. The process of claim 10, wherein the inhibitors are added during step II and reach a concentration in a process stream upstream of the ISU of from 1-100000 parts per million.

17. The process of claim 14, wherein:
a) the reactive monomers are selected from the group consisting of: styrene; (meth)acrylic acid; (meth)acrylic acid esters; acrylonitrile; butadiene; isoprene; chloroprene; vinyl acetate; ethylene; and propylene; and/or
b) the inhibitors are selected from the group consisting of: hydroxylamines; oximes; sterically hindered stable nitroxyl radicals; quinone methide inhibitors; nitroaromatics; nitrosoaromatics; benzoquinones; hydroquinones; phenothiazines; phenolic antioxidants; N,N'-dialkyl-p-phenylene diamines; and N,N'-dialkyl-p-benzoquinone diimides.

18. The process of claim 10, wherein:
a) the reactive monomers are selected from the group consisting of: styrene; (meth)acrylic acid; (meth)acrylic acid esters; acrylonitrile; butadiene; isoprene; chloroprene; vinyl acetate; ethylene; and propylene; and/or
b) the inhibitors are selected from the group consisting of: hydroxylamines; oximes; sterically hindered stable nitroxyl radicals; quinone methide inhibitors; nitroaromatics; nitrosoaromatics; benzoquinones; hydroquinones; phenothiazines; phenolic antioxidants; N,N'-dialkyl-p-phenylene diamines; and N,N'-dialkyl-p-benzoquinone diimides.

19. The process of claim 10, wherein said process is carried out using an apparatus comprising:
a) at least one inhibitor feed port;
b) a primary purification unit "PPU", separating a feed stream comprising reactive monomers into "RM-stream 1", enriched in reactive monomers and "RM-depleted stream," depleted in reactive monomers, wherein "enriched" means that the concentration of the reactive monomer in RM-stream 1 is higher than in the feed stream of the PPU and "depleted" means, that the concentration of the reactive monomers in the RM-depleted stream is lower than in the feed stream of the PPU;
c) an inhibitor separation unit "ISU", separating RM-stream 1, or an intermediate modified RM-stream 1, into "RM-stream 2", enriched in the reactive monomer, and an "inhibitor stream," enriched in inhibitors and depleted in reactive monomers, wherein enriched means that the concentration of reactive monomers in RM stream 2 is higher than in the feed stream of the ISU and that the concentration of inhibitors in the inhibitor stream is higher than in the feed stream of the ISU;
and wherein the apparatus is designed such that the "inhibitor stream" is recycled to at least one inhibitor feed port, and the ISU is a membrane separation unit comprising OSN nanofiltration membranes having a molecular weight cut off from 150 to 900 g/mol.

20. The process of claim 19, wherein said process is used on a stream of reactive monomer raw material comprising, at least one reactive monomer selected from the group consisting of styrene, (meth)acrylic acid and (meth)acrylic acid esters, acrylonitrile, butadiene, isoprene, chloroprene, vinyl acetate, ethylene and propylene.

* * * * *